(12) United States Patent
Dell

(10) Patent No.: US 7,771,471 B2
(45) Date of Patent: Aug. 10, 2010

(54) FLOATING OPTIC ACCOMMODATING INTRAOCULAR LENS

(75) Inventor: Steven J. Dell, Austin, TX (US)

(73) Assignee: C & C Vision International Limited, Dublan (IE)

( * ) Notice: Subject to any disclaimer, the term of this patent is extended or adjusted under 35 U.S.C. 154(b) by 90 days.

(21) Appl. No.: 11/357,930

(22) Filed: Feb. 17, 2006

(65) Prior Publication Data

US 2006/0259140 A1    Nov. 16, 2006

Related U.S. Application Data

(60) Provisional application No. 60/681,115, filed on May 13, 2005.

(51) Int. Cl.
*A61F 2/16* (2006.01)
(52) U.S. Cl. .................. 623/6.37; 623/6.38; 623/6.4; 623/6.44; 623/6.46
(58) Field of Classification Search .................. None
See application file for complete search history.

(56) References Cited

U.S. PATENT DOCUMENTS

| | | | |
|---|---|---|---|
| 4,174,543 A | 11/1979 | Kelman | |
| 4,244,060 A | 1/1981 | Hoffer | |
| 4,254,509 A | 3/1981 | Tennant | |
| 4,254,510 A | 3/1981 | Tennant | |
| 4,298,996 A | 11/1981 | Barnet | |
| 4,304,012 A | 12/1981 | Richard | |
| 4,409,691 A | 10/1983 | Levy | |
| 4,424,597 A | 1/1984 | Schlegel | |
| 4,441,217 A | 4/1984 | Cozean, Jr. | |
| 4,477,931 A | 10/1984 | Kelman | |
| 4,573,998 A | 3/1986 | Mazzocco | |
| 4,585,457 A | 4/1986 | Kalb | |
| 4,605,411 A | 8/1986 | Fedorov et al. | |
| 4,629,462 A | 12/1986 | Feaster | |
| 4,664,666 A | 5/1987 | Barrett | |
| 4,673,406 A | 6/1987 | Schlegel | |
| 4,704,123 A | 11/1987 | Smith | |
| 4,718,904 A | 1/1988 | Thornton | |
| 4,738,680 A | 4/1988 | Herman | |
| 4,753,655 A | 6/1988 | Hecht | |
| 4,759,761 A | 7/1988 | Portnoy | |

(Continued)

FOREIGN PATENT DOCUMENTS

EP    0208546 A    1/1987

(Continued)

OTHER PUBLICATIONS

Archimede Busacca, Ciliary Muscle Physiology Studied by Gonioscopy, Annals of Oculistics, vol. CLXXXVIII, Jan. 1955 (English Translation).

(Continued)

*Primary Examiner*—David H Willse
*Assistant Examiner*—Javier G Blanco
(74) *Attorney, Agent, or Firm*—Orrick, Herrington & Sutcliffe LLP

(57) ABSTRACT

An accommodating intraocular lens comprising a flexible body and flexible optic, and a flexible skirt connecting the optic to the body. The body may have extending loop haptics.

10 Claims, 3 Drawing Sheets

U.S. PATENT DOCUMENTS

| | | | |
|---|---|---|---|
| 4,764,169 A | 8/1988 | Grendahl | |
| 4,778,463 A | 10/1988 | Hetland | |
| 4,813,955 A | 3/1989 | Achatz et al. | |
| 4,816,030 A | 3/1989 | Robinson | |
| 4,840,627 A | 6/1989 | Blumenthal | |
| 4,842,601 A | 6/1989 | Smith | |
| 4,880,427 A | 11/1989 | Anis | |
| 4,892,543 A | 1/1990 | Turley | |
| 4,932,966 A | 6/1990 | Christie et al. | |
| 4,932,970 A | 6/1990 | Portney | |
| 4,963,148 A | 10/1990 | Sulc et al. | |
| 4,994,082 A | 2/1991 | Richards et al. | |
| 5,047,051 A | 9/1991 | Cumming | |
| 5,078,742 A | 1/1992 | Dahan | |
| 5,141,507 A | 8/1992 | Parekh | |
| 5,171,319 A | 12/1992 | Keates et al. | |
| 5,171,320 A | 12/1992 | Nishi | |
| 5,217,490 A | 6/1993 | Sayano et al. | |
| 5,275,624 A | 1/1994 | Hara et al. | |
| 5,376,115 A | 12/1994 | Jansen | |
| 5,476,514 A | 12/1995 | Cumming | |
| 5,496,366 A | 3/1996 | Cumming | |
| 5,522,891 A | 6/1996 | Klaas | |
| 5,578,078 A | 11/1996 | Nakajima et al. | |
| 5,674,282 A | 10/1997 | Cumming | |
| 5,964,802 A * | 10/1999 | Anello et al. | 623/6.4 |
| 6,051,024 A | 4/2000 | Cumming | |
| 6,129,760 A | 10/2000 | Fedorov et al. | |
| 6,193,750 B1 | 2/2001 | Cumming | |
| 6,197,059 B1 | 3/2001 | Cumming | |
| 6,387,126 B1 | 5/2002 | Cumming | |
| 6,494,911 B2 | 12/2002 | Cumming | |
| 6,540,353 B1 | 4/2003 | Dunn | |
| 6,551,354 B1 | 4/2003 | Ghazizadeh et al. | |
| 6,554,859 B1 | 4/2003 | Lang et al. | |
| 6,558,419 B1 | 5/2003 | Pham et al. | |
| 6,638,306 B2 | 10/2003 | Cumming | |
| 6,660,035 B1 * | 12/2003 | Lang et al. | 623/6.37 |
| 6,767,363 B1 | 7/2004 | Bandhauer | |
| 7,150,760 B2 * | 12/2006 | Zhang | 623/6.37 |
| 2001/0001836 A1 | 5/2001 | Cumming | |
| 2002/0065556 A1 | 5/2002 | Cumming | |
| 2002/0128710 A1 | 9/2002 | Eggleston | |
| 2003/0060880 A1 | 3/2003 | Feingold | |
| 2003/0065387 A1 | 4/2003 | Callahan et al. | |
| 2003/0187505 A1 | 10/2003 | Liao | |
| 2004/0002757 A1 | 1/2004 | Lai et al. | |
| 2004/0243233 A1 | 12/2004 | Phillips | |
| 2006/0116764 A1 | 6/2006 | Simpson | |

FOREIGN PATENT DOCUMENTS

| | | |
|---|---|---|
| EP | 0336877 A1 | 10/1989 |
| EP | 0941717 A | 9/1999 |
| EP | 1462071 A2 | 9/2004 |
| FR | 1103399 | 11/1955 |
| GB | 2171912 A | 9/1986 |
| WO | WO 95/06446 | 3/1995 |
| WO | WO 96/16734 A2 | 5/1996 |
| WO | WO 99/29266 A1 | 6/1999 |
| WO | WO 03/082147 A2 | 10/2003 |
| WO | WO 2004/004606 A2 | 1/2004 |

OTHER PUBLICATIONS

Archimede Busacca, La Physiologid Du Muscle Ciliarire Etudiee par la Gonioscopie, Annales D'Oculistique, vol. CLXXXVIII, 1st Livraison, Janvier 1955 (French Translation).

D. Jackson Coleman, M.D., On the Hydraulic Suspension Theory of Accommodation, Tr. Am. Opth. Soc. vol. LXXXIV, pp. 846-868, 1986.

J. Stuart Cumming, M.D., Accommodating Intra-Ocular Lens Development & Clinical Results, PowerPoint presentation 1999-2000.

Spencer Thornton, "Accommodating in Pseudophakia," Color Atlas of Lens Implantation, Chapter 25, pp. 159-161.

Lee, Judith, "Update on IOLs," Outpatient Surgery (Mar. 2002), printed Oct. 26, 2004 (http://www.outpatientsurgery.net/2002/os03/f4.shtml).

Zhang, Z. et al., "A clinical study of posterior capsular opacification after implantation of foldable intraocular lenses with different edges of optics," Zhonghua Yan Ke Za Zhi 38(10):606-609 (Oct. 2002), printed Oct. 26, 2004 (http://www.ncbi.nlm.nih.gov/entrez/query.fcgi?cmd=Retrieve&db=pubmed&dopt=Abstract&list...).

Masket, Samuel, "Continuing Medical Education: Oct. 2003 IOL Edge Design, and PCO Dysphotopsia," Review of Ophthalmology, printed Oct. 26, 2004 (http://www.revophth.com/index.asp?ArticleType=SiteSpec&page=cme/oct03/lesson.htm).

Sabbagh, Leslie, "IOL Design Closes Off PCO," Review of Ophthalmology, printed Oct. 26, 2004 (http://www.revophth.com/index.asp?page=1_255.htm).

* cited by examiner

FLOATING OPTIC ACCOMMODATING INTRAOCULAR LENS

BACKGROUND

This application claims priority to U.S. Provisional Application Ser. No. 60/681,115, filed on May 13, 2005. Priority to the prior application is expressly claimed, and the disclosure of the application is hereby incorporated by reference in its entirety.

Intraocular lenses have for many years had a design of a single optic with loops attached to the optic to center the lens and fixate it in the empty capsular bag of the human lens. In the mid '80s plate lenses were introduced, which comprised a silicone lens, 10.5 mm. in length, with a 6 mm. optic. These lenses could be folded but did not fixate well in the capsular bag, but resided in pockets between the anterior and posterior capsules. The first foldable lenses were all made of silicone. In the mid 1990s an acrylic material was introduced as the optic of lenses. The acrylic lens comprised a biconvex optic with a straight edge into which were inserted loops to center the lens in the eye and fixate it within the capsular bag.

Recently accommodating intraocular lenses have been introduced to the market, which generally are modified plate haptic lenses and, like the silicone plate haptic lenses, have no clear demarcation between the junction of the plate with the optic's posterior surface. A plate haptic lens may be defined as an intraocular lens having two or more plate haptics where combined junctions with the optic represent one quarter or more of the circumference of the optic.

Flexible acrylic material has gained significant popularity among ophthalmic surgeons. In 2003 more than 50% of the intraocular lenses implanted had acrylic optics. Hydrogel lenses have also been introduced. Both the acrylic and hydrogel materials are incapable of multiple flexions without fracturing.

The advent of an accommodating lens which functions by moving along the axis of the eye by repeated flexions somewhat limited the materials from which the lens could be made. Silicone is the ideal material, since it is flexible and can be bent probably several million times without showing any damage. Additionally a groove or hinge can be placed across the plate adjacent to the optic as part of the lens design to facilitate movement of the optic relative to the outer ends of the haptics. An example accommodating lens is disclosed in U.S. Pat. No. 6,387,126 in the name of J. Stuart Cumming.

SUMMARY OF THE INVENTION

According to the present invention a new form of accommodating intraocular lens is provided which can be thought of as including a "floating optic piston" with a 360 degree broad and weak skirt essentially allowing the optic to move anteriorly and posteriorly in a piston fashion in response to the pressure gradient created with accommodation.

Thus, it is a feature of the present invention to provide a new form of accommodating lens.

DESCRIPTION OF PREFERRED EMBODIMENT

Figure 1:
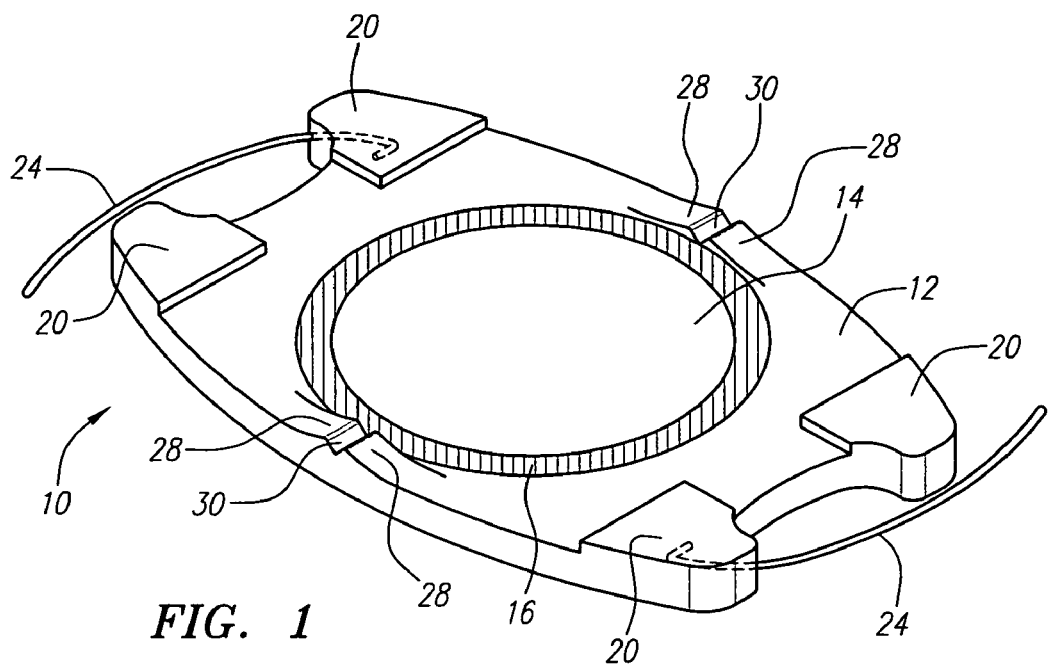
FIG. 1 is a prospective view of the front or anterior side of the lens according to the present invention.
Figure 2:
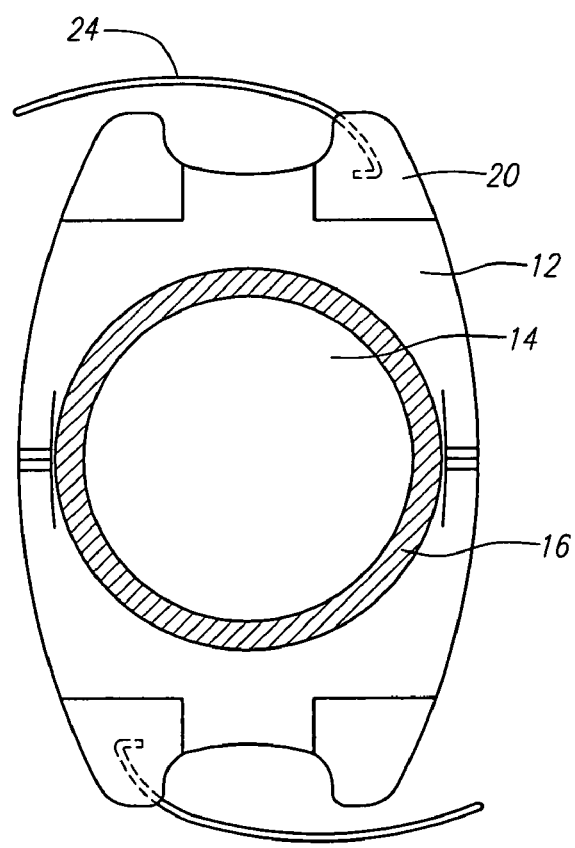
FIG. 2 is a plan view thereof.
Figure 3:
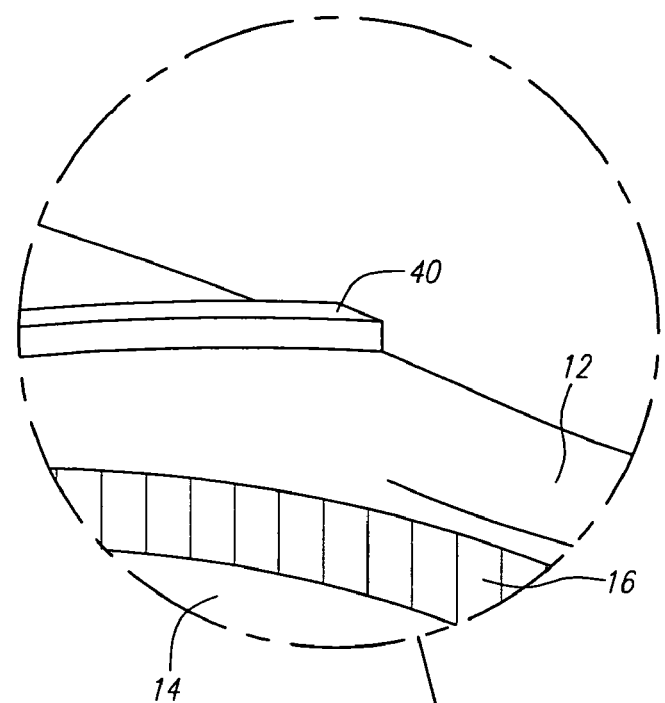
FIG. 3 is a detailed view of the bottom or posterior side of the lens particularly illustrating ridges to prevent posterior capsular opacification.
Figure 3:
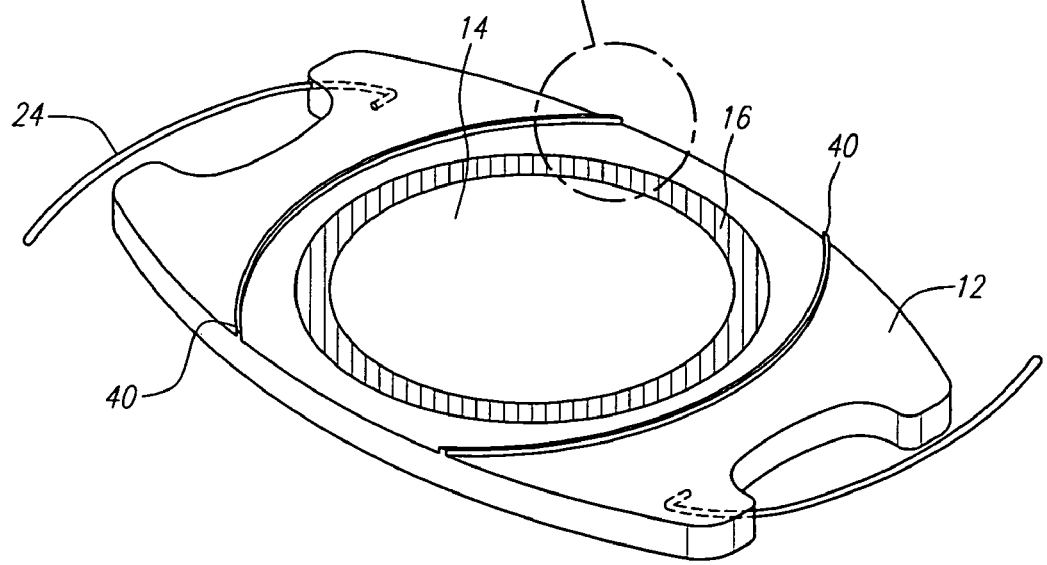
Figure 4:
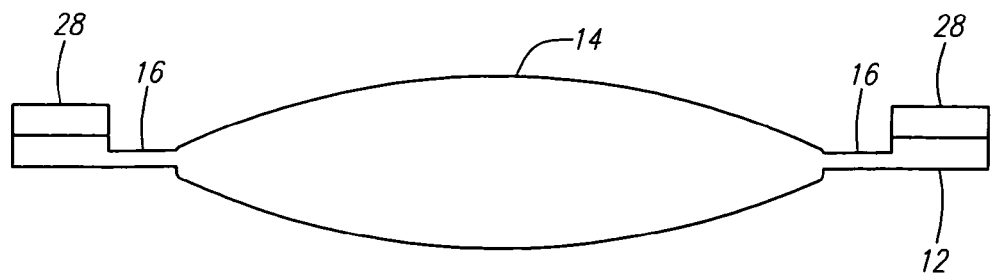
FIG. 4 is a diagrammatic cross-sectional view through the middle of the lens at its thickest part along the short axis to particularly illustrate a vault meter.
Figure 5:
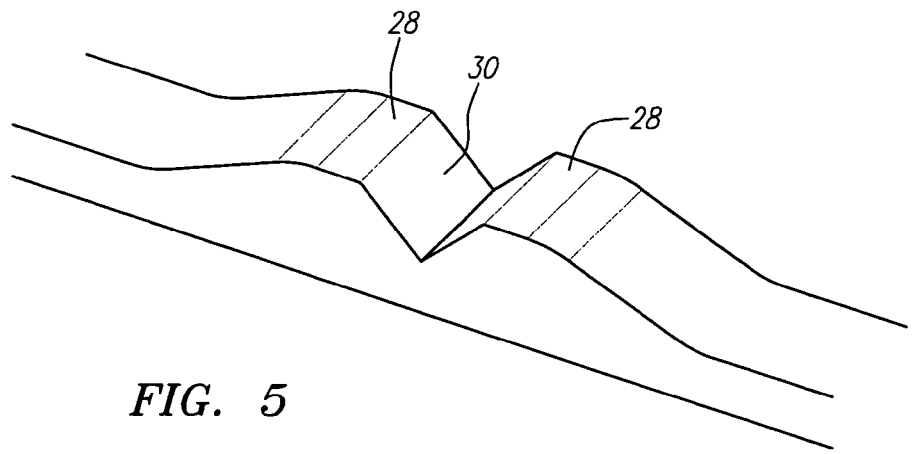
FIG. 5 is an enlarged detailed view of the vault meter.

Turning now to the drawings, FIG. 1 is a perspective view of the present lens 10 including a lens body or plate 12 and optic 14. The body 12 and optic 14 are of silicone or other suitable flexible material. A flexible skirt 16 is between the body 12 and the periphery or outer diameter of the optic 14. The flexible skirt may be 0.4 mm wide and 0.1 mm thick so as to essentially create an "optic piston" 14. The optic piston 14 typically can have a diameter of 4.5 mm, a typical width of the lens 10 on the short side is 6.3 mm and the typical length from end to end on the long side is 10.5 mm. The body 12 and optic 14, as well as outer thickened footplates 20 are formed of silicone or other suitable flexible material. The lens 10 also includes loops 24 of polymide or similar material. The outer loop to loop length is 11.5 mm to 13.0 mm.

The skirt 16 functions as a pseudo-zonular complex, allowing the optic to move anteriorly and posteriorly. The 0.4 mm wide annular skirt is a point of relative weakness in the plane of the lens encircling the optic 14, thereby allowing the entire optic 14 to herniate forward (anteriorly) from its far posterior position in a translational forward movement. This feature is enhanced by keeping the mass of the optic 14 to a minimum as described below. This new mechanism may boost the effect of the other features of the lens. Rather than a fluid-filled sac pushing through an aperture as in some prior lenses, the present lens involves a deformable solid optic moving anteriorly through a weak area (16) in the plate or body 12.

Capsular contraction is inevitable in some eyes with any design, and it is not believed to be the case with this lens; however, the lens may be prone to over-vaulting in the event of aggressive capsular contraction syndrome (CCS). Therefore, an optional feature is included which amounts to a thickening of the edge of the plate 12 over the short axis of the lens as indicated at 28 along with a V-shaped opening 30 anteriorly which doubles as a "vault-meter," indicating the degree of posterior vault. Thus, if the lens begins to bow too posteriorly, the V opening 28 closes and prevents against exaggerated posterior flexure in the event of CCS. The angle of the V opening 30 should be about 50 degrees so as to close and block further vaulting at about 50 degrees of flexure to prevent over-vaulting given that the cord length of the capsular bag shrinks to a minimum of about 8 mm post-op. (Reference: Capsule measuring ring to predict capsular bag diameter and follow its course after foldable intraocular lens implantation. Tehrani M, Dick H B, Krummenauer F, Pfirrmann G, Boyle T, Stoffelns B M; Cataract Refract Surge 2003: 29: 2127-34). There is an additional function of these thickened areas of the plate. They also serve to elevate the anterior capsule away from the optic and from the posterior capsule. This may serve to reduce capsular opacification and contraction.

Another feature allowing the present lens to accommodate is that the optic 14 can be deformable and constructed with a lower durometer than previously built into any lens. The surrounding plate 12 preferably is made of a higher, standard durometer material, similar to the eyeonics AT45 lens (which is durometer 48). The optic 14 itself is not required to contribute to the structural stability of the lens and, therefore, the optic 14 can be extremely soft. In addition to forward axial translation, the bending or deformation of the optic 14 with accommodation will induce power change. This may result in the bending of the lens to be accentuated. This feature is further enhanced by maintaining the optic very thin since a thinner optic will bend more than a thick optic for any given level of force applied. An example range of optic center thicknesses is about 0.3 mm to 1.1 mm. A 4.5 mm diameter optic 14 and with a reduced edge thickness of 0.1 to 0.2 mm for example can be provided. The index of refraction can be increased and this will accentuate this feature even further. The fact that this optic 14 is symmetrically tethered to the plate 12 in all meridians can mean that power changes in the curvature are also symmetrical, meaning spherical power change as opposed to astigmatic changes found in some other lenses. Optic flexure is a new and poorly understood phenomenon, and optical distortion may be encountered either at near or far distances, in which case the durometer of the material will need to be raised.

The present lens can be easily foldable with forceps or an injector. A pre-loaded system is preferable.

Figure 6A:
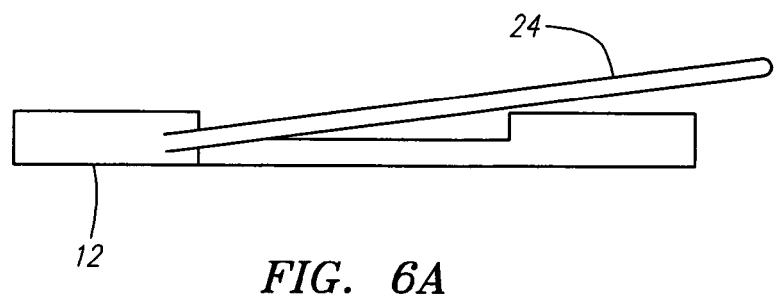
FIG. 6A and FIG. 6B are end views of the lens showing two haptic options.
Figure 6B:
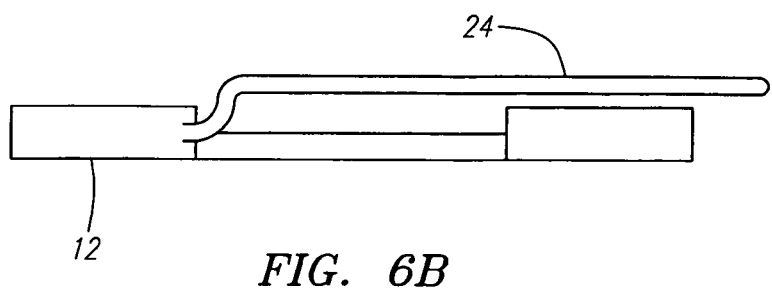

Turning to the haptics 24, these represent a modification of an old C40 IOL design, but it has been altered to allow the lens to fixate in the equator of the capsular bag with complete certainty, but also to be removed or even in the late post-op period by "dialing" (e.g., rotating) the lens out of the capsular bag. The loops 24 may be slightly angulated forward (anteriorly) as seen in FIGS. 6A-6B, thereby decreasing the likelihood of an anterior vault. This can eliminate the need for cycloplegia post-op. The broad plate 12 structure of the lens 10 allows for excellent protection against vitreous herniation in the event of a YAG centrally or peripherally for CCS. Two optional loop 24 haptics are shown in FIGS. 6A and 6B.

An additional feature is the incorporation of a ridge or ridges 40 on the under surface (posterior side) of the plate 12 (or haptic arm as the case may be). These ridges traverse the plate from side to side. The purpose of these ridges is to prevent proliferation of lens epithelial cells behind the plate or haptic. For plate lenses this can dramatically reduce the incidence of capsular contraction as lens equatorial lens epithelial cells will be prevented from migrating under the plate and undergoing a fibrotic contraction. Furthermore, the square edge of the plate haptics protect against cells migrating in from the sides of the plate, but these traversing ridges 40 are the only way to block equatorial cells from migrating centrally under the plates.

While an embodiment of the present invention as been shown and described, various modifications may be made without departing from the scope of the present invention, and all such modifications and equivalents are intended to be covered.

What is claimed is:

1. An uniplanar accommodating intraocular lens comprising a flexible hinged body having ends, and a flexible floating optic attached to the lens body by a flexible annular single thin flat skirt which is continuously attached to the entire periphery of the optic and which allows the optic to move anteriorly and posteriorly in a piston fashion automatically in response to the pressure gradient created in the vitreous cavity with accommodation, the body having a central V- shaped area across the body between the ends thereof, the body comprising a plurality of loops attached to said ends of the body, and posterior ridges to prevent cell migration along the back surface of the body, wherein the lens body comprises flat plate haptics completely surrounding and suspending said flexible floating optic.

2. A lens as in claim 1 wherein the V-shaped area of the body comprises a vault meter.

3. An uniplanar accommodating intraocular lens comprising a flexible hinged body having ends and a flexible floating optic, the flexible optic being mounted to the body by a annular single thin flat skirt which is continuously attached to the entire periphery of the optic and which allows the optic to move anteriorly and posteriorly in a piston fashion automatically in response to the pressure gradient created in the vitreous cavity with accommodation, the body having a central V-shaped area across the body between the ends thereof, the skirt being approximately 0.4 mm wide and approximately 0.1 mm thick, a plurality of loops attached to said ends of the body, and posterior ridges to prevent cell migration along the back surface of the body, wherein the lens body comprises flat plate haptics completely surrounding and suspending said flexible floating optic.

4. A lens as in claim 3 wherein the V-shaped area is for indicating the degree of posterior vault.

5. A lens as in claim 3 wherein the loops are slightly angulated anteriorly.

6. An uniplanar accommodating intraocular lens comprising a flexible hinged lens body completely surrounding and suspending a flexible floating optic and attached to the optic by a thin flat annular skirt which is continuously attached to the entire periphery of the optic and which allows the optic to move anteriorly and posteriorly in a piston fashion automatically in response to the pressure gradient created in the vitreous cavity with accommodation, the lens body having V-shaped hinges across the body between ends thereof, and loops to allow the lens to fixate and center within the capsular bag of the eye and to allow easy removal of the lens from the bag, and posterior ridges to prevent cell migration along the back surface of the body, wherein the lens body comprises flat plate haptics.

7. An uniplanar accommodating intraocular lens comprising a flexible hinged body and a flexible floating optic mounted within the lens body by a flat annular skirt which is continuously attached to the entire periphery of the optic and which allows the optic to move anteriorly and posteriorly in a piston fashion automatically in response to the pressure gradient created in the vitreous cavity with accommodation, the lens body opposite the optic center of the optic having two V-shaped structures on each side of the optic designed to restrict posterior vaulting of the lens body, and posterior ridges to prevent cell migration along the back surface of the body, wherein the lens body comprises flat plate haptics completely surrounding and suspending said flexible floating optic.

8. An accommodating intraocular lens as in claim 7 wherein the structures are vault meters.

9. An uniplanar accommodating intraocular lens comprising a flexible hinged body having ends and a flexible floating optic, the flexible optic being attached to the lens body by an annular single thin flat skirt which is continuously attached to the entire periphery of the optic and which allows the optic to move anteriorly and posteriorly in a piston fashion automatically in response to the pressure gradient created in the vitreous cavity with accommodation, the skirt being approximately 0.4 mm wide and approximately 0.1 mm thick, a central V-shaped area across the body between the ends thereof, wherein said V-shaped area comprises a vault meter, a plurality of loops attached to the ends of the body, and posterior ridges to prevent cell migration along the back surface of the body, wherein the lens body comprises flat plate haptics completely surrounding and suspending said flexible floating optic.

10. A lens as in claim 9, wherein the loops are slightly angulated anteriorly.

* * * * *